(12) United States Patent
Oginski et al.

(10) Patent No.: US 8,414,531 B2
(45) Date of Patent: Apr. 9, 2013

(54) HANDHELD DEVICE FOR THE LOCAL PUNCTURING OF A HUMAN OR AN ANIMAL SKIN, DRIVE UNIT, NEEDLE UNIT AND METHOD FOR COUPLING

(75) Inventors: Stefan Oginski, Berlin (DE); Kornelius Knothe, Berlin (DE)

(73) Assignee: MT.DERM GmbH, Berlin (DE)

( * ) Notice: Subject to any disclaimer, the term of this patent is extended or adjusted under 35 U.S.C. 154(b) by 24 days.

(21) Appl. No.: 12/533,973

(22) Filed: Jul. 31, 2009

(65) Prior Publication Data

US 2010/0036317 A1      Feb. 11, 2010

(51) Int. Cl.
 *A61B 17/34*  (2006.01)
 *A61M 5/20*  (2006.01)

(52) U.S. Cl.
USPC ............ 604/131; 604/159; 606/185; 606/186

(58) Field of Classification Search .................. 604/131, 604/164.01, 164.04, 164.12, 158–159; 600/564, 600/566–567; 606/167, 185–186
See application file for complete search history.

(56) References Cited

U.S. PATENT DOCUMENTS

| | | | | |
|---|---|---|---|---|
| 5,279,552 A | * | 1/1994 | Magnet | 604/47 |
| 5,471,102 A | * | 11/1995 | Becker et al. | 310/50 |
| 5,776,158 A | * | 7/1998 | Chou | 606/186 |
| 6,689,095 B1 | * | 2/2004 | Garitano et al. | 604/70 |
| 7,380,480 B1 | * | 6/2008 | Chen | 81/9.22 |
| 2002/0069726 A1 | * | 6/2002 | Adler et al. | 81/9.22 |
| 2003/0195542 A1 | * | 10/2003 | Lee | 606/186 |
| 2004/0116953 A1 | * | 6/2004 | Dixon | 606/186 |
| 2006/0020283 A1 | * | 1/2006 | Lisec | 606/185 |
| 2008/0033470 A1 | | 2/2008 | Kluge et al. | |
| 2010/0191268 A1 | * | 7/2010 | Lee | 606/185 |

FOREIGN PATENT DOCUMENTS

| | | |
|---|---|---|
| DE | 19836376 A1 | 2/2000 |
| DE | 19945334 A1 | 4/2001 |
| EP | 1882491 A1 | 1/2008 |
| WO | 2008018781 A | 2/2008 |

\* cited by examiner

*Primary Examiner* — Quynh-Nhu H Vu
(74) *Attorney, Agent, or Firm* — Smith Patent Office

(57) ABSTRACT

The invention relates to a handheld device for the local puncturing of a human or an animal skin, in particular for the introduction of an active substance or for the application of a tattoo or a permanent make-up, comprising a drive unit which is configured so as to produce a repetitive drive movement, and a needle unit which comprises a needle device and is configured so as to couple to the drive unit in such a manner that the repetitive drive movement for the extension and retraction of the needle device can be coupled into the latter, said drive unit having formed on it a displaceable actuating element which is functionally coupled to a needle connection device, and said needle unit having formed on it a functional member which is assigned to the actuating element, said actuating element and said functional member being configured so as to move the actuating element from a first displacement position to a second displacement position by means of the assigned functional member when coupling the needle unit to the drive unit, thus moving the needle connection device to a coupling position in which the needle device can be coupled to the needle connection device for purposes of operation. Furthermore, the invention relates to a method for coupling a needle unit to a drive unit on a handheld device, a drive unit for a handheld device as well as a needle unit for a handheld device.

14 Claims, 11 Drawing Sheets

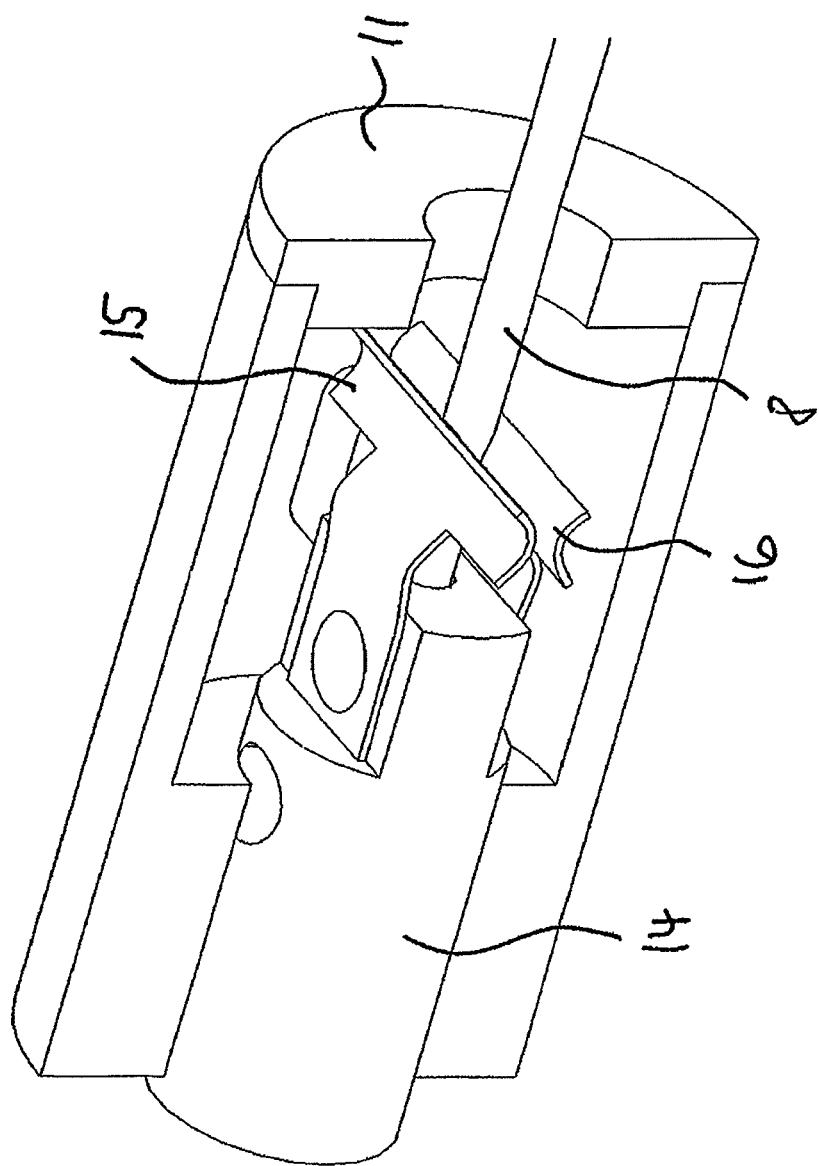

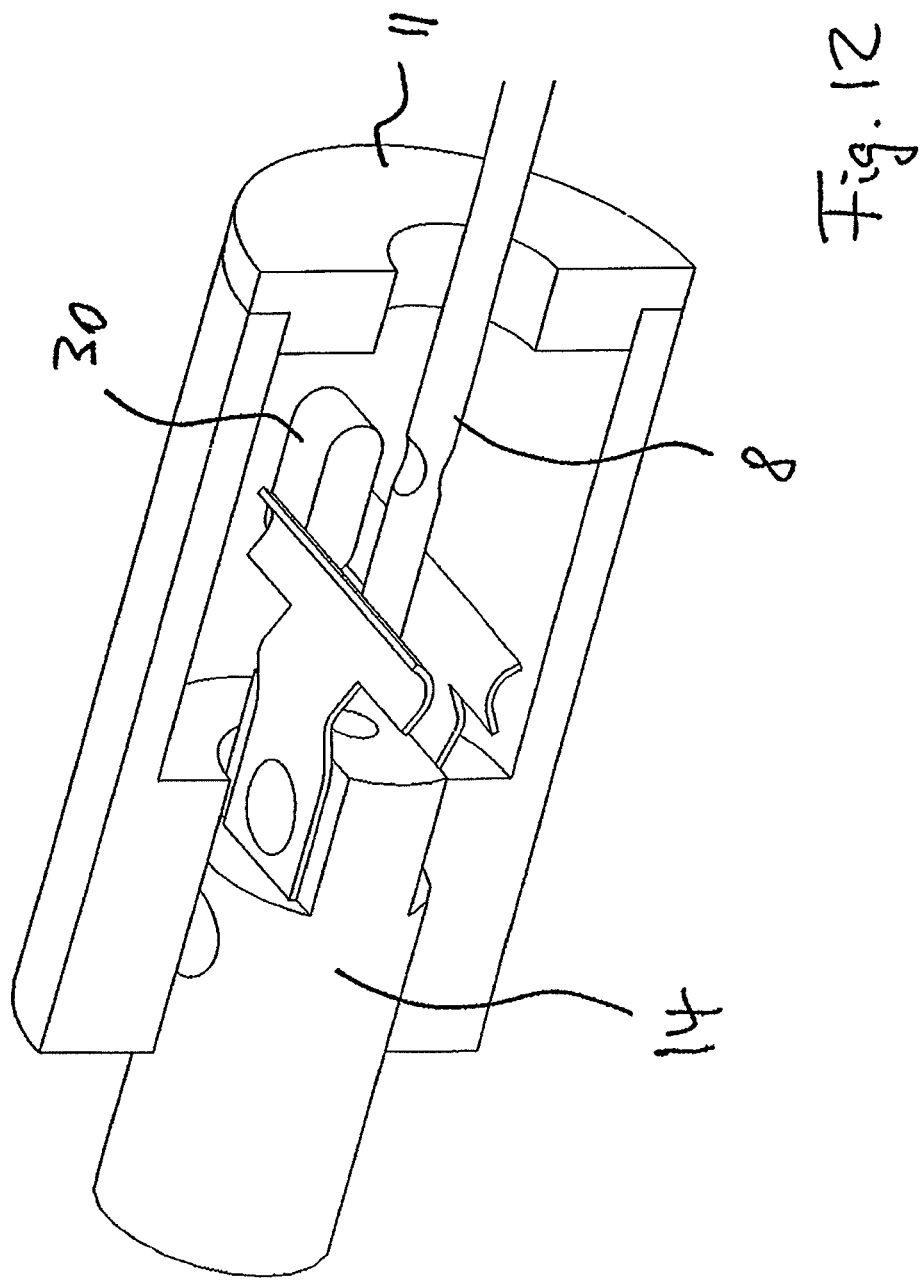

HANDHELD DEVICE FOR THE LOCAL PUNCTURING OF A HUMAN OR AN ANIMAL SKIN, DRIVE UNIT, NEEDLE UNIT AND METHOD FOR COUPLING

The invention relates to a handheld device for the local puncturing of a human or an animal skin, in particular for the introduction of an active substance or for the application of a tattoo or a permanent make-up, and to a drive unit and a needle unit for the handheld device and a method for coupling the needle unit to the drive unit.

BACKGROUND OF THE INVENTION

Such handheld devices are used for the local puncturing of a human or an animal skin by means of a repetitive extension and retraction movement of a needle member which may comprise one or more needles. Subsequently, any material may be introduced into the skin in the area of the puncture, in particular colorants, cosmetic substances or pharmaceutically active agents. The repetitive extension and retraction movement is typically effected at a high frequency.

Known handheld devices for the local puncturing of a skin have a drive unit which, on its part, comprises drive means producing the repetitive drive movement. Said repetitive drive movement can be transferred to the needle element by connecting a needle device comprising the needle element to a needle connection device.

SUMMARY OF THE INVENTION

The object of the invention is to state and present new technologies for a handheld device for the local puncturing of a human or an animal skin, which technologies allow the drive unit and the needle unit of the handheld device to be coupled and uncoupled in a manner that ensures the function of the handheld device and a user-friendly operation.

This object is achieved according to the invention by a handheld device described herein. Furthermore, there are provided a method for coupling a needle unit to a drive unit on the handheld device as well as a drive unit for the handheld device and a needle unit for the handheld device.

The invention encompasses the conceptual idea of a handheld device for the local puncturing of a human or an animal skin comprising a drive unit which is configured so as to produce a repetitive drive movement, and a needle unit which comprises a needle device and is configured so as to couple to the drive unit in such a manner that the repetitive drive movement for the extension and retraction of the needle device can be coupled into the latter, said drive unit having formed on it a displaceable actuating element which is functionally coupled to a needle connection device, and said needle unit having formed on it a functional member which is assigned to the actuating element, said actuating element and said functional member being configured so as to move the actuating element from a first displacement position to a second displacement position by means of the assigned functional member when coupling the needle unit to the drive unit, thus moving the needle connection device to a coupling position in which the needle device can be coupled to the needle connection device for purposes of operation.

According to a further aspect of the invention, a method for coupling the needle unit to a drive unit on the handheld device has been developed, said method comprising the following steps: provision of a drive unit which is configured so as to produce a repetitive drive movement, provision of a needle unit which comprises a needle device and is configured so as to couple to the drive unit in such a manner that the repetitive drive movement for the extension and retraction movement of the needle device can be coupled into the latter, and coupling of the needle unit to the drive unit by moving a displaceable actuating element of the drive unit, which is functionally coupled to a needle connection device, from a first displacement position to a second displacement position by means of a functional member of the needle unit which is assigned to the actuating element, thus moving the needle connection device to a coupling position in which the needle device is coupled to the needle connection device for purposes of operation.

Furthermore, a drive unit for a handheld device is developed, said drive unit comprising drive means which are configured so as to produce a repetitive drive movement, a needle connection device and a displaceable actuating element which is functionally coupled to the needle connection device and configured so as to move the actuating element from a first displacement position to a second displacement position when a needle unit having formed on it a functional member which is assigned to the actuating element is coupled to said drive unit, thus moving the needle connection device to a coupling position in which a needle device encompassed by the needle unit can be coupled to the needle connection device for purposes of operation.

At last, a needle unit for a handheld device is developed which comprises a needle device and a functional member, said functional member being assigned to a displaceable actuating element of a drive unit which can be coupled to said needle unit and being configured so as to move the actuating element from a first displacement position to a second displacement position when the needle unit is coupled to the drive unit, thus moving a needle connection device encompassed by the drive unit to a coupling position in which the needle device can be coupled to the needle connection device for purposes of operation.

The invention ensures in a simple but reliable manner that the needle connection device, which, on its part, constitutes the coupling point for the needle device of the needle unit in the drive unit, is reliably moved to the coupling position during the coupling process, in which coupling position the needle device can be coupled to the needle connection device for purposes of operation. The actuating element which is functionally coupled to the needle connection device and the functional member which is formed on the needle unit and assigned to the actuating element cooperate as a coupling mechanism in order to move the needle connection device to the coupling position during the coupling process, in which coupling position the needle device can be coupled to the needle connection device.

The functional member formed on the needle unit may be formed as a stop element, for example, which is brought into contact with the actuating element when the needle unit is coupled to the drive unit and moves said actuating element to the second displacement position. Such a stop mechanism can be realized particularly easily by a mechanical stop element. Alternatively or complementarily other mechanisms may be used for the cooperation of the assigned functional member and the actuating element, such as a magnetic mechanism which causes the actuating element to move from the first displacement position to the second displacement position.

A preferred development of the invention provides that the actuating element is configured so as to move automatically from the second displacement position to the first displacement position when the needle unit is uncoupled from the drive unit, thus moving the needle connection device to an uncoupling position in which the needle device can be uncoupled from the needle connection device. The self-acting backward movement of the actuating element can be reached, for example, by providing a spring tension by means of a spring element. The actuating element is moved from the first displacement position to the second position against the spring force. When the needle unit is uncoupled from the drive unit, the spring force in this embodiment causes the actuating element, which, on its part, is functionally coupled to the needle connection device, to move back in its initial position.

One development of the invention advantageously provides that the drive unit and the needle unit are configured so as to form a positive or form-fit coupling connection. Such a positive connection supports, for example, a secure seat of the needle unit on the drive unit. Moreover, it ensures in a possible embodiment a functionally reliable and correct configuration of drive unit and needle unit relative to each other, so that the needle unit is functionally mounted to the drive unit. Independent of the positive coupling connection or in combination with it, a guiding mechanism may be provided which guides the needle unit when it is coupled to the drive unit, for example by means of a nose on the drive unit which engages into a guiding recess on the needle unit which is formed on an internal surface of a housing of the needle unit, for example.

In an advantageous embodiment of the invention it may be provided that the needle unit comprises a proximal section on which is formed the assigned functional member and which is configured so as to couple to the drive unit, and a distal section in which is formed a needle opening through which a needle element of the needle device can be retracted and extended. The needle unit with the proximal and the distal sections is preferably made in one piece. In one embodiment, the housing of the needle unit is made elastically deformable in the area of the proximal section, for example as a plastic housing which allows the user to deform the proximal section by finger pressure, so that an easier coupling and uncoupling of the needle unit or the execution of the coupling process is possible in the first place. In one embodiment, for example, a latching connection between the needle unit and the drive unit may be released by elastically deforming the proximal section by finger pressure.

A preferred development of the invention provides that the proximal section and the distal section are detachably connected to each other. By means of this type of construction it is possible, for example, to realize an embodiment of the handheld device in which, firstly, the proximal section is coupled to the drive unit, to which purpose the actuating element and thus the needle connection device is actuated. Subsequently, in this embodiment, the distal section with the needle device can be connected to the drive unit, for example by snapping or screwing it on. In doing this, also the needle device is coupled to the needle connection device which is in the coupling position. A further embodiment provides that the proximal section of the needle unit may take two latching positions on the drive unit, so that the associated actuating element of the drive unit takes the first latching position when the proximal section takes the first latching position, and that the associated actuating element of the drive unit takes the second latching position when the proximal section takes the second latching position. This causes the needle connection device to move to the coupling/uncoupling position when the proximal section of the needle unit is in the second/first latching position. This allows the distal section of the needle unit to be detached from the proximal section or connected thereto when the proximal section is in the first latching position. Thus, the distal section can be replaced while the proximal section of the needle unit remains connected to the drive unit.

An advantageous embodiment of the invention provides that the proximal section is fixed to the drive unit when the needle unit is coupled to the drive unit. The fixation may be realized, for example, by means of a latching mechanism or a stop mechanism.

In a purposeful embodiment of the invention, it may be provided that the proximal section is guided on a housing of the drive unit during the coupling process of the needle unit and the drive unit. The guidance is realized, for example, by means of a combination of a nose and a guide groove receiving said nose.

An advantageous embodiment of the invention provides that the actuating element is configured so as move between the first and the second displacement position in the direction of a coupling movement carried out by the needle unit during the coupling process of the needle unit and the drive unit. In a preferred embodiment, the coupling movement is a rectilinear movement.

A further development of the invention preferably provides that the actuating element is mounted in a guiding device on the drive unit which is configured so as to guide the actuating element when moving from the first to the second displacement position. The guidance of the actuating element is carried out, for example, by means of a guiding device formed on the housing of the drive unit, for example by means of components mounted in such a manner that they are displaceable within each other. In one embodiment, the actuating element is formed as a cylindrical sleeve which is displaceable relative to housing sections of the drive unit, for example by means of a sliding movement. In this or other embodiments, the actuating element may be designed as a housing element of the drive unit.

A preferred development of the invention provides that the needle connection device is formed with a mechanical connection mechanism for the needle device. In one embodiment, said connection mechanism may be a spring force connection mechanism, for example, with which the needle device is held in the needle connection device by means of spring force clamping. However, other clamping mechanisms may also be used. Alternatively or complementarily a coupling which involves a magnet mechanism, for example, may also be provided. Such a magnet mechanism can be provided by means of permanent magnets or electromagnets.

In one embodiment, the needle connection device has clamping elements or fixation elements which are assigned to each other and displaceable relative to each other, and which are moved relative to each other when the actuating element is actuated, so that the needle connection device takes different functional positions. The relative movement of the clamping elements or fixation elements can be realized by means of spreading elements which are manufactured, for example, in the form of movable or stationary plungers or noses. The change-over between the functional positions of the clamping elements is preferably reached by means of a movement in the direction of the coupling movement. In one embodiment, the needle connection device may be configured, independent of its precise design, so as to form a positive connection between the needle device and the needle connection device when they are coupled to each other.

In a preferred embodiment of the invention, there is at least one wedge-shaped plunger provided which is configured to actuate the clamping elements or fixation elements.

One advantageous embodiment of the invention provides that the needle connection device is configured so as to rigidly couple to the needle device. In a possible embodiment, this means in particular that both the shear force for the extension of the needle device and the return force for the retraction of the needle device are coupled via the needle connection device on the needle device and thus directly on the needle element, for example by means of a positive or form-fit connection. This also eliminates undesired rattling during the operation of the handheld device. In this context, the form-fit connection between the needle connection device and the needle device, for example, is of advantage, the latter possibly having a correspondingly configured needle shaft for this purpose. A form-fit connection may be formed, for example, by means of recesses on the needle shaft and functional members on the needle connection device engaging therein. Alternatively or complementarily, a force-fit connection or a frictional connection may be formed which may be realized, for example, by spring elements which radially push the needle connection device. Thanks to the acting clamping force and the existing friction between the spring element and the needle device, the coupling can transmit the forces necessary for applying a tattoo in an axial direction.

A preferred development of the invention provides that the needle device in the needle unit is mounted in a guiding element which holds the needle device in an initial position when the needle unit is coupled to the drive unit. Said guiding element which is made, for example, of an elastic material is formed, for instance, by means of a diaphragm which encompasses the needle element. The function of the guiding element is to position the needle device in the unit in such a way that a reliable coupling of the needle device to the needle connection device is possible. The positioning forces which are necessary for the positioning are, however, extremely small and lie in the range of the weight of the needle device. The guiding element therefore needs to be designed with a correspondingly low rigidity only. Due to the low positioning forces, it has practically no influence on the repetitive movement during the application of the tattoo and allows a free movement of the needle element during the operation of the handheld device so that the extension and retraction movements of the needle element are essentially not subject to reactions by the guiding element. In one embodiment, the diaphragm has, to this end, a dome-shaped cross-section in which the wall of the diaphragm lowers again towards the center. Furthermore, the guiding element serves at the same time as a seal opposite the outlet opening in the needle unit. This assures that the material to be introduced into the skin or blood escaping from the skin does not pass from the area behind the outlet opening in other sections of the needle unit or the drive unit during the operation of the handheld device. In another embodiment, a combination of a sliding seal through which the needle element is extended and retracted and a weak spring which positions the needle device for the coupling process can be used instead of a resilient diaphragm of low rigidity.

One development of the invention preferably provides that the needle unit is designed as a disposable unit. If the needle unit is composed of sections which are separable or detachable from each other, it may be provided that only the distal section with the needle element is designed as a disposable article.

The method for coupling the needle unit to the drive unit on the handheld device as well as the needle unit and the drive unit may be designed according to one or more of the previously described embodiments.

DESCRIPTION OF PREFERRED EMBODIMENTS OF THE INVENTION

In the following, the invention is described in greater detail by way of preferred embodiments with reference to the figures of drawings, in which.

Figure 1:
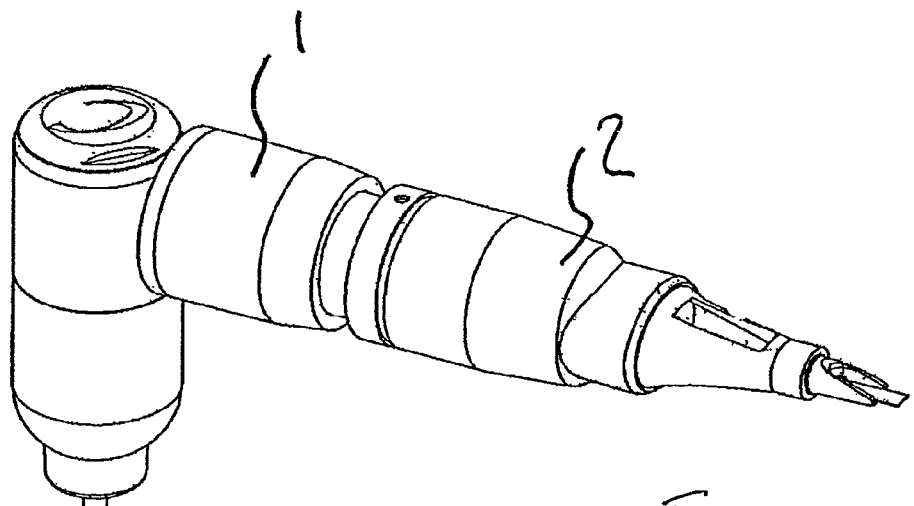
FIG. 1 is a perspective view of a handheld device on which a needle unit is coupled to a drive unit.
Figure 5:
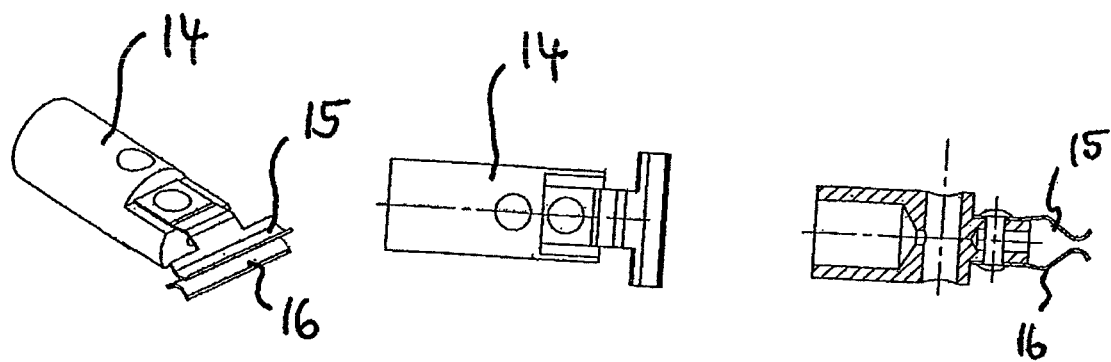
Figure 6:
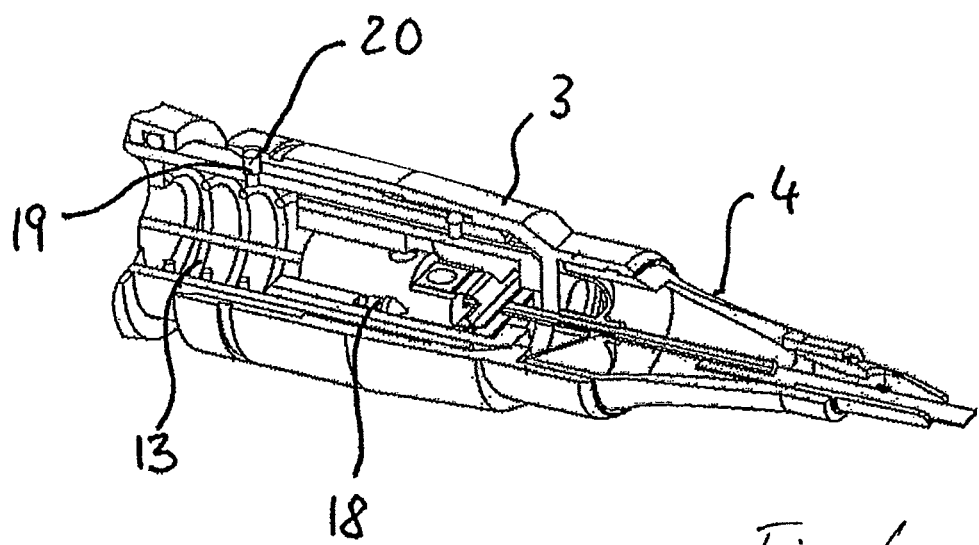
Figure 7:
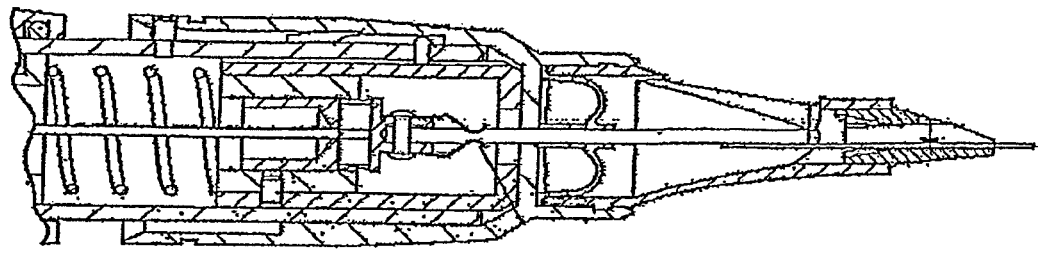
Figure 13:
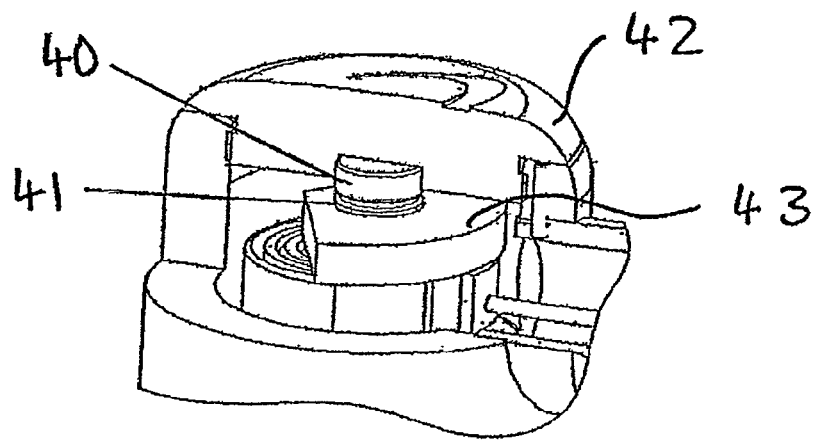
Figure 8:
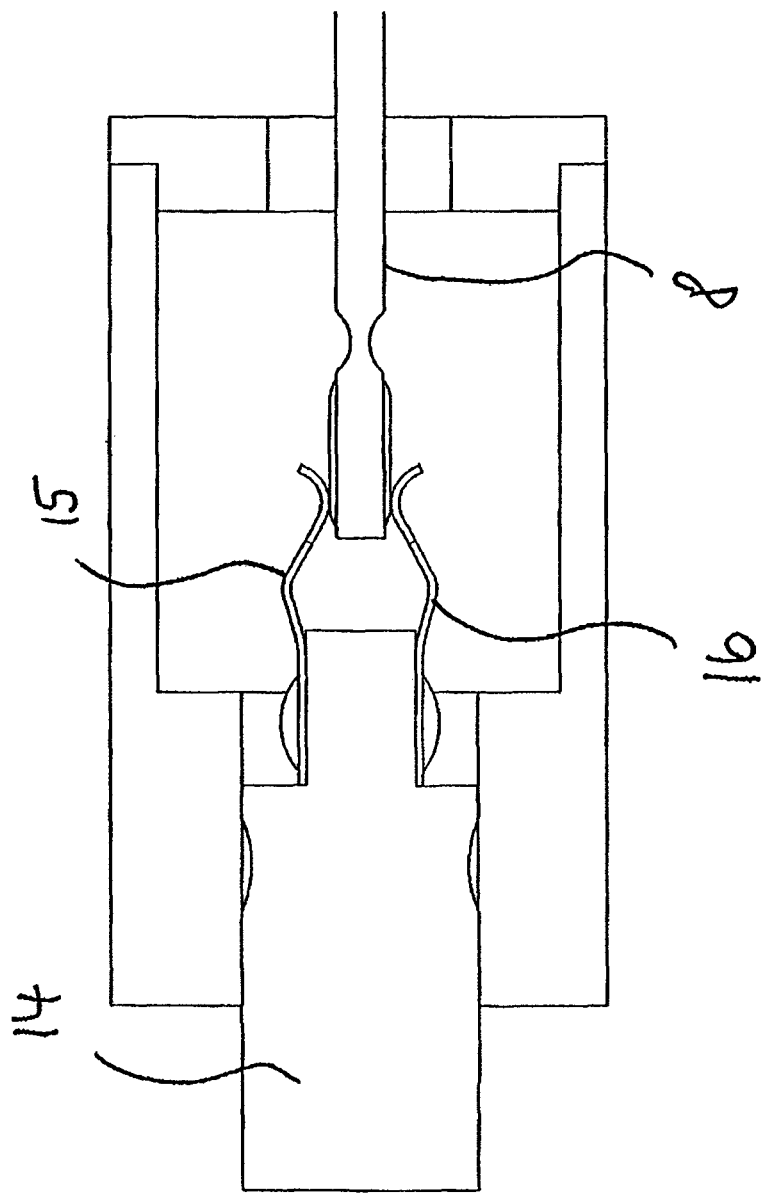
Figure 9:
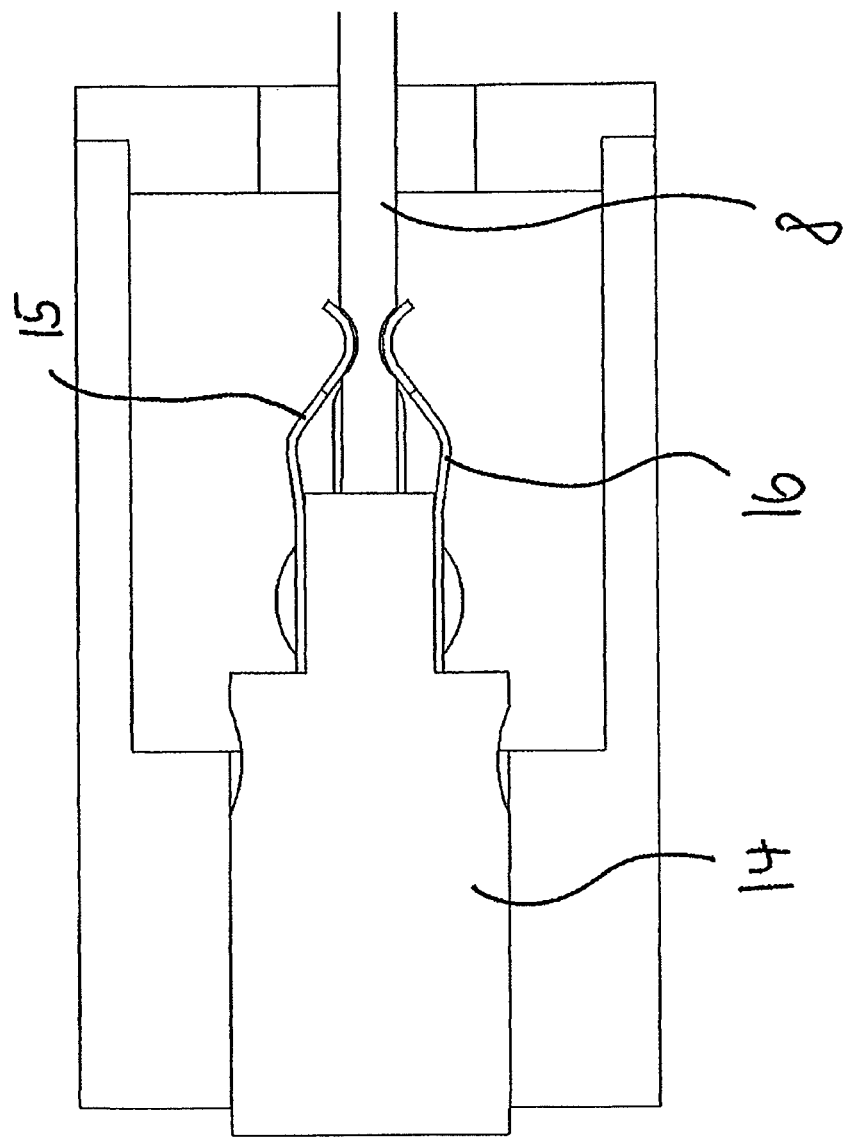
Figure 10:
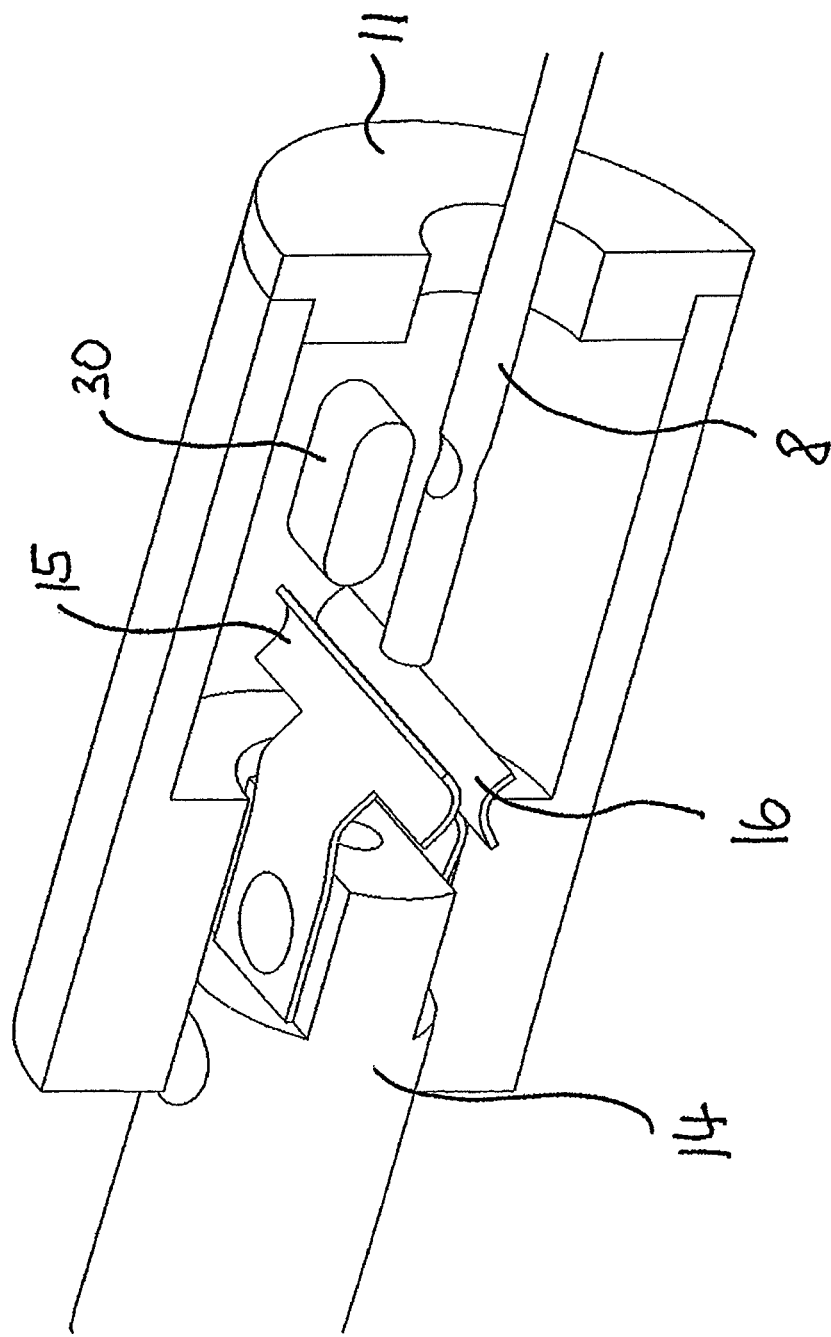
Figure 14:
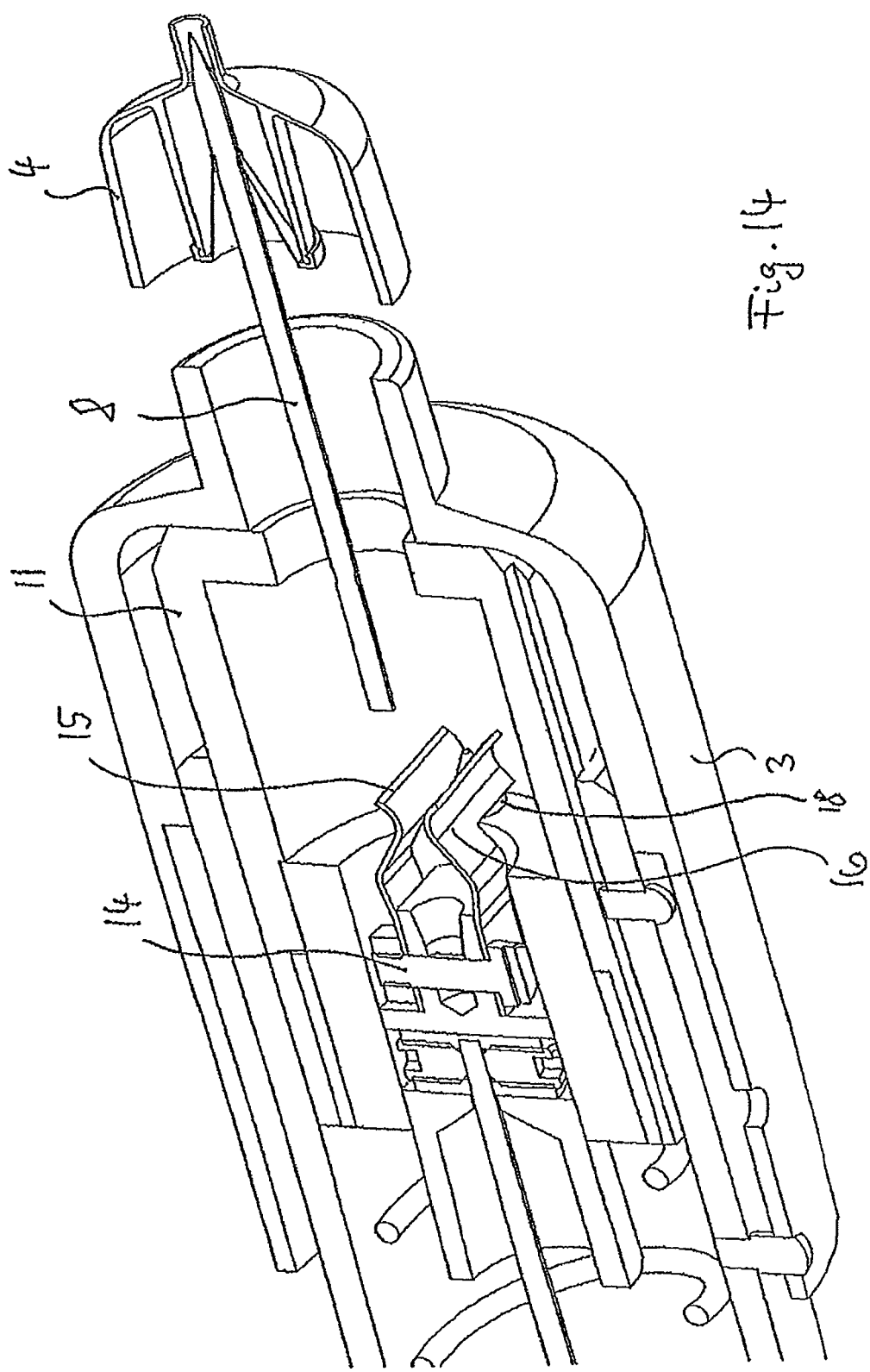
Figure 15:
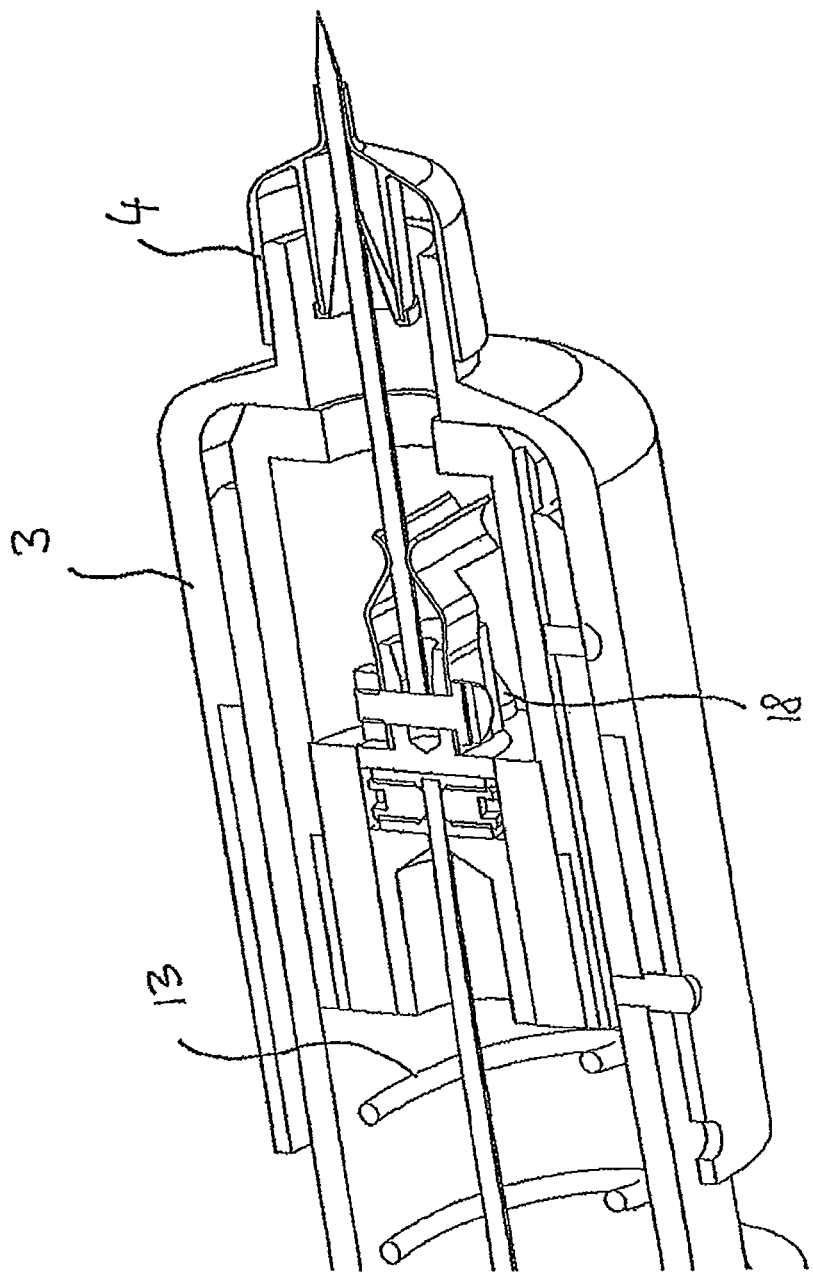

FIG. 5 presents multiple illustrations of a needle connection device of the handheld device according to FIG. 1;

FIG. 6 is a perspective elevation view of a section of the handheld device according to FIG. 1 in the coupled state;

FIG. 7 is a sectional view of the section of the handheld device of FIG. 6;

FIG. 8 is an enlarged detail view showing the coupling process of the needle device;

FIG. 9 is an enlarged view of the needle connection device with the needle device coupled thereto;

FIG. 10 is a perspective view with the needle connection device and the actuating element according to another embodiment;

FIG. 11 is a perspective view of a configuration of FIG. 10 in the coupled state;

FIG. 12 is a perspective view of the configuration of FIG. 10 with the needle connection device being in an uncoupling position;

FIG. 13 is a perspective view of a section of the drive unit;

FIG. 14 is a perspective view of a section of a handheld device comprising a needle unit which consists of several parts; and FIG. 15 is a further perspective view of the section of the handheld device according to FIG. 15.

Figure 2:
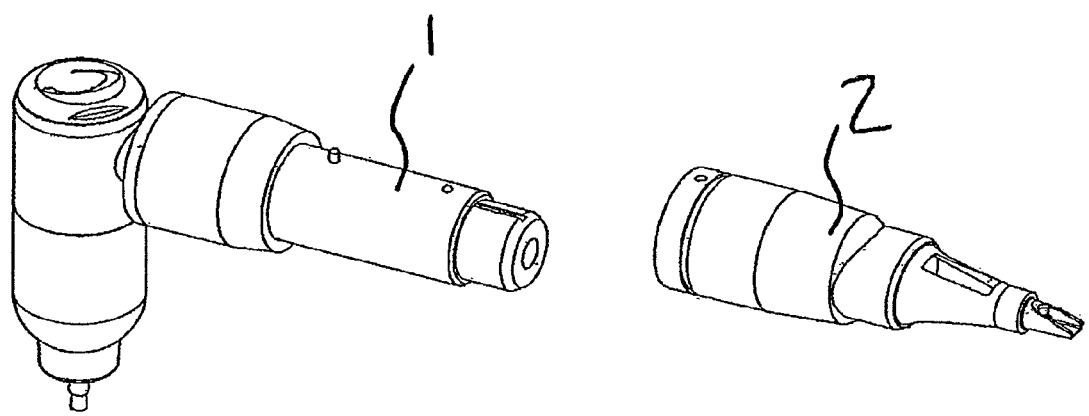
FIG. 2 is a perspective view of the handheld device of FIG. 1, with the needle unit being uncoupled from the drive unit.
Figure 3:
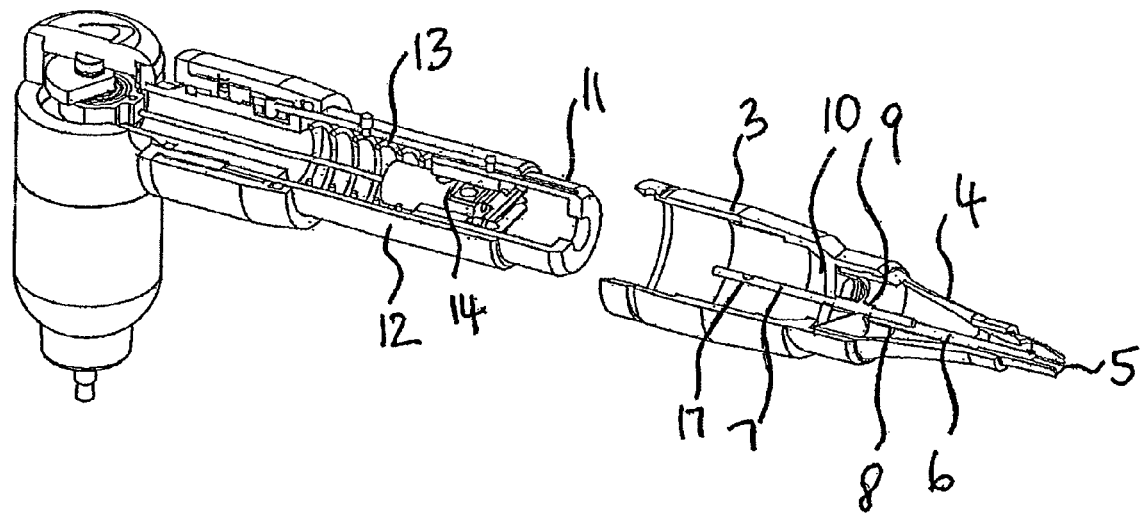
FIG. 3 is a perspective elevation view of the handheld device according to FIG. 2 in the uncoupled state.

FIG. 1 shows a perspective view of a handheld device for the local puncturing of a human or an animal skin in which a drive unit 1 is coupled to a needle unit 2. FIG. 2 shows a perspective view of the handheld device of FIG. 1, with the needle unit 2 being uncoupled from the drive unit 1. FIG. 3 shows a perspective elevation view of the handheld device according to FIG. 2 in the uncoupled state.

The needle unit 2 has a proximal section 3 which, independent of its precise design, may also be designated as coupling section, as well as a distal section 4 which, independent of its precise design, may also be designated needle receiving section and in which is formed a needle opening 5 through which a needle element 6 can be extended and retracted. Said needle element 6, which may be composed of one or more needles, is, on its part, housed in a needle shaft 7 which forms together with the needle element 6 a needle device 8. Said needle device 8 is guided by means of a diaphragm 9. Said diaphragm 9 is made of an elastic material and holds the needle device 8 in an initial position when the latter is in the uncoupled state shown in FIG. 3. During operation, that is when the drive unit 1 and the needle unit 2 are connected to each other and a repetitive drive movement is produced by the drive unit 1, the diaphragm 9 fixed to the needle device 8 is stretched without producing active forces which counter the drive movement during the operation.

Figure 4:
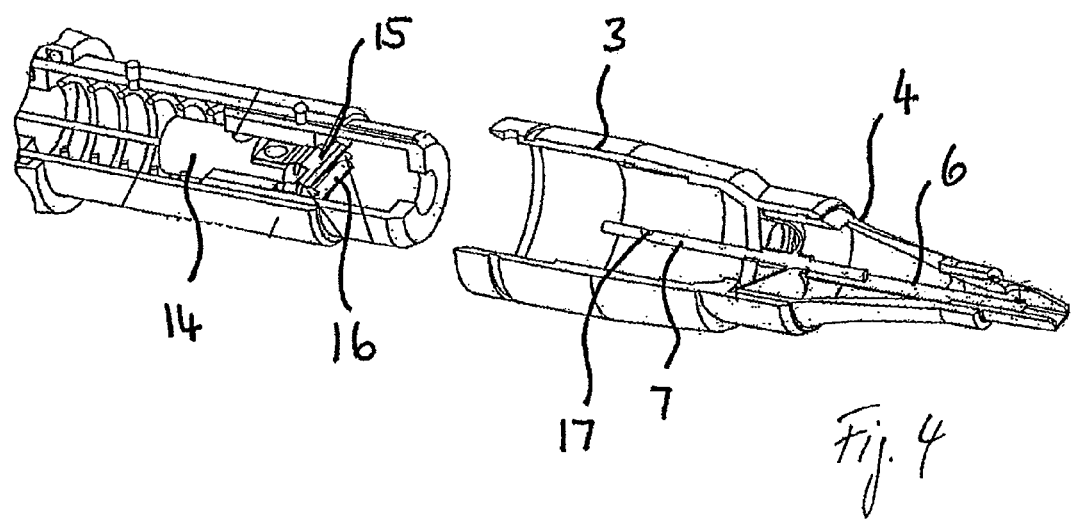
FIG. 4 is a perspective elevation view of a section of the handheld device according to FIG. 1 in the uncoupled state.

A functional member 10 which is designed as a stop element is formed on the proximal section 3 of the needle unit 2. Said functional member 10 cooperates with an actuating element 11 during the coupling process of the needle unit 2 and the drive unit 1, which becomes clearer in the FIGS. 4, 6 and 7 below.

In the illustrated embodiment, the actuating element 11 is formed as a cylindrical sleeve which is displaceably mounted in a housing section 12. The displacement of the actuating element 11 from a first displacement position which is shown in FIG. 3 and corresponds to an extended position to a retracted position (see FIGS. 6 and 7) is carried out against the preload of a spring element 13 during the coupling process of the needle unit 2 and the drive unit 1.

The actuating member 11 is functionally coupled to a needle connection device 14 arranged in the housing section 12 in such a way that the needle connection device 14 is actuated when the actuating element 11 is inserted so that the needle connection device 14 moves to a coupling position which is shown in FIG. 5 for the needle connection device 14. In the coupling position, functional members 15, 16 which are designed as clamping elements or fixation elements are, according to FIG. 5, arranged opposite each other and at a distance from each other which allows the needle shaft 7 to couple thereto so that the functional members 15, 16 engage positively into a recess 17 on the needle shaft 7, which can be seen in particular in FIG. 7.

The functional members 15, 16 of the needle connection device 14 move to the coupling position shown in FIG. 5 when the actuating element 11 is inserted during the coupling process of the needle unit 2 by retracting wedge-shaped plungers 18 which are firmly connected to the actuating element 11, which can, in particular, be seen in FIG. 6. During this, the proximal section 3 of the needle unit 2 is moved onto the housing section 12 until, according to FIG. 6, a holding pin 19 engages into a borehole 20 in the proximal section 3 of the needle unit, thus fixing the needle unit 2 to the drive unit 1. To release it from this fixed position, the proximal section 3 can be elastically deformed by means of finger pressure of the user, so that the borehole 20 disengages from the holding pin 19, thus allowing the needle unit 2 to be removed. During this uncoupling process, the actuating element which is driven by the spring element 13 returns to the position shown in FIG. 3. FIG. 3 also shows that the wedge-shaped plungers 18 then force apart the functional members 15, 16 of the needle connection device 14, so that the needle device 8 can be released from the needle connection device 14.

Contrary to the illustration shown in FIG. 6, the diaphragm 9 is deformed and stretched in the coupled state illustrated there, since it sits firmly on the needle shaft 7.

FIG. 8 shows an enlarged detailed representation during the coupling process of the needle device 8 to the needle connection device 14. FIG. 9 shows an enlarged representation of the needle connection device 14 with the needle device coupled thereto.

FIG. 10 shows a perspective representation with the needle connection device 14 and the actuating element 11 according to another embodiment. In contrast to the embodiment in the FIGS. 3, 4, 6 and 7, the functional members 15, 16 of the needle connection device 14 are forced apart by means of a nose 30 which, on its part, is arranged on the actuating element 11.

FIG. 11 shows a perspective representation of the arrangement of FIG. 10 in the coupled state.

FIG. 12 shows a perspective representation of the arrangement of FIG. 10, with the needle connection device 14 being in an coupling or uncoupling position and the nose 30 forcing apart the functional members 15, 16.

FIG. 13 shows a perspective representation of a section of the drive unit 1. There are integrated two diametrally magnetized magnet 40, 41. An upper magnet 40 is embedded in a housing cover 42. A lower magnet 41 is arranged in a flywheel 43. The two magnets 40, 41 are oriented in such a way that, in the position of the flywheel mass shown in FIG. 13, opposed magnetic poles face each other. If the electric motor of the drive unit 1 stops in another position, the two magnets 40, 41 produce a torque sufficient to rotate the flywheel mass, in the currentless state, in the position shown in FIG. 13, so that the needle element 6 is retracted. There is therefore no risk of injury in the switched-off state of the drive unit 1.

FIGS. 14 and 15 show perspective representations of a handheld device in which the needle unit 2 consists of several parts. The proximal section 3 is separable from the distal section 4. During the coupling process of the needle unit 2 and the drive unit 1, the proximal section 3 can be coupled to the drive unit 1 first, so that the actuating element 11 is actuated (see FIG. 14). Subsequently, the distal section 4 with the needle device 8 is snapped on (see FIG. 15).

Furthermore, in the embodiment shown in FIG. 14, the proximal section 3 of the needle unit 2 can take two latching positions on the drive unit 1, such that the actuating element 11 of the drive unit 1 takes at the same time the first displacement position when the proximal section 3 takes the first latching position, and that the associated actuating element 11 of the drive unit takes at the same time the second displacement position when the proximal section 3 takes the second latching position. This causes the needle connection device 8 to move to the coupling/uncoupling position when the proximal section 3 of the needle unit 2 is in the second and first latching position, respectively. This allows the distal section 4 of the needle unit to be detached from the proximal section 3 or connected thereto when the proximal section 3 is in the first latching position. Thus, the distal section 4 can be replaced while the proximal section 3 of the needle unit 2 remains connected to the drive unit 1.

The features of the invention disclosed in the preceding description, the claims and the designs may be of importance for the realization of the invention in its different embodiments both individually and in any combination.

The invention claimed is:

1. A handheld device for the local puncturing of a human or an animal skin, in particular for the introduction of an active substance or for the application of a tattoo or a permanent make-up, comprising:
   a drive unit which is configured so as to produce a repetitive drive movement; and
   a needle unit which comprises a needle device and is configured so as to couple to the drive unit in such a manner that the repetitive drive movement for the extension and retraction of the needle device can be coupled into the drive unit;
   wherein said drive unit includes a displaceable actuating element that is coupled to a needle connection device, and said needle unit having a functional member which is a stop element that contacts the displaceable actuating element, said displaceable actuating element and said stop element being configured so as to move the displaceable actuating element from a first displacement position to a second displacement position by the stop element when coupling the needle unit to the drive unit, thus moving the needle connection device to a coupling position in which the needle device can be coupled or uncoupled to the needle connection device.

2. The handheld device according to claim 1, wherein the displaceable actuating element is configured so as to move automatically from the second displacement position to the first displacement position when the needle unit is uncoupled from the drive unit, thus moving the needle connection device to an uncoupling position in which the needle device can be uncoupled from the needle connection device.

3. The handheld device according to claim 1, wherein the drive unit and the needle unit are configured so as to form a positive coupling connection.

4. The handheld device according to claim 1, wherein the needle unit comprises a proximal section on which is formed the stop element and the proximal section is configured so as to couple to the drive unit, and a distal section connected thereto in which is formed a needle opening through which a needle element of the needle device can be retracted and extended.

5. The handheld device according to claim 4, wherein the proximal section and the distal section are detachably connected to each other.

6. The handheld device according to claim 4, wherein the proximal section is fixed to the drive unit when the needle unit is coupled to the drive unit.

7. The handheld device according to claim 4, wherein the proximal section is guided on a housing of the drive unit during the coupling process of the needle unit and the drive unit.

8. The handheld device according to claim 1, wherein the displaceable actuating element is configured so as to move between the first and the second displacement position in the direction of a coupling movement carried out by the needle unit during the coupling process of the needle unit and the drive unit.

9. The handheld device according to claim 1, wherein the displaceable actuating element is mounted in a guiding device on the drive unit which is configured so as guide the displaceable actuating element when moving from the first to the second displacement position.

10. The handheld device according to claim 1, wherein the needle connection device is formed with a mechanical connection mechanism for the needle device.

11. The handheld device according to claim 10, wherein the needle connection device has clamping elements or fixation elements which are assigned to each other and displaceable relative to each other.

12. The handheld device according to claim 11, further comprising at least one wedge-shaped plunger configured to actuate the clamping elements or fixation elements.

13. The handheld device according to claim 1, wherein the needle connection device is configured so as to rigidly couple to the needle device.

14. The handheld device according to claim 1, wherein the needle device in the needle unit is mounted in a guiding element which holds the needle device in an initial position when the needle unit is coupled to the drive unit.

* * * * *